United States Patent
Zarkadas et al.

(10) Patent No.: US 9,784,699 B2
(45) Date of Patent: Oct. 10, 2017

(54) QUANTITATIVE X-RAY ANALYSIS—MATRIX THICKNESS CORRECTION

(71) Applicant: PANalytical B.V., Almelo (NL)

(72) Inventors: Charalampos Zarkadas, Almelo (NL); Milen Gateshki, Almelo (NL); Alexander Kharchenko, Almelo (NL); Waltherus Van Den Hoogenhof, Almelo (NL); Petronella Emerentiana Hegeman, Almelo (NL); Dick Kuiper, Almelo (NL)

(73) Assignee: PANALYTICAL B.V., Almelo (NL)

( * ) Notice: Subject to any disclaimer, the term of this patent is extended or adjusted under 35 U.S.C. 154(b) by 255 days.

(21) Appl. No.: 14/636,950

(22) Filed: Mar. 3, 2015

(65) Prior Publication Data
US 2016/0258890 A1 Sep. 8, 2016

(51) Int. Cl.
G01N 23/22 (2006.01)
G01N 23/223 (2006.01)
G01N 23/20 (2006.01)

(52) U.S. Cl.
CPC ... *G01N 23/2206* (2013.01); *G01N 23/20083* (2013.01); *G01N 23/223* (2013.01); *G01N 2223/401* (2013.01)

(58) Field of Classification Search
CPC ............ G01N 2223/076; G01N 23/207; G01N 23/2206; G01N 23/223; G01N 23/20083
See application file for complete search history.

(56) References Cited

U.S. PATENT DOCUMENTS

| 4,803,715 A | * | 2/1989 | Cho | ................. | G01N 23/20083 |
| | | | | | 378/89 |
| 5,970,116 A | * | 10/1999 | Dueholm | ................. | G01N 9/24 |
| | | | | | 378/54 |

(Continued)

FOREIGN PATENT DOCUMENTS

| EP | 0816834 | 1/1998 |
| EP | 2377467 | 10/2011 |
| GB | 2476255 | 6/2011 |

OTHER PUBLICATIONS

Rafal Sitko, "Quantitative X-ray fluorescence analysis of samples of less than 'infinite thickness':Difficulties and possibilities", Sep. 30, 2009, Elsevier, Part B, 1161-1172.*

*Primary Examiner* — David J Makiya
*Assistant Examiner* — Soorena Kefayati
(74) *Attorney, Agent, or Firm* — Leason Ellis LLP

(57) ABSTRACT

Quantitative X-ray analysis is carried out by making X-ray fluorescence measurements to determine the elemental composition of a sample and a correction measurement by measuring the transmitted intensity of X-rays at an energy E transmitted directly through the sample without deviation. An X-ray diffraction measurement is made in transmission by directing X-rays from an X-ray source at the energy E onto a sample at an incident angle $\psi_1$ to the surface of the sample and measuring a measured intensity $I_d(\theta_{fl})$ of the diffracted X-rays at the energy E with an X-ray detector at an exit angle $\psi_2$ corresponding to an X-ray diffraction peak of a predetermined component. A matrix corrected X-ray intensity is obtained using the measured X-ray intensity in the X-ray diffraction measurement, the correction measurement and the mass attenuation coefficient of the sample calculated from the elemental composition and the mass attenuation coefficients of the elements.

13 Claims, 4 Drawing Sheets

(56) References Cited

U.S. PATENT DOCUMENTS

| | | | | |
|---|---|---|---|---|
| 6,829,327 B1* | 12/2004 | Chen | ................... | G01N 23/223 |
| | | | | 378/44 |
| 7,646,847 B2* | 1/2010 | He | ...................... | G01N 23/207 |
| | | | | 378/71 |
| 8,433,035 B2* | 4/2013 | Watanabe | ............ | G01N 23/223 |
| | | | | 378/44 |
| 9,188,553 B2* | 11/2015 | Sakuta | ................. | G01N 23/223 |
| 9,448,190 B2* | 9/2016 | Yun | .................... | G01N 23/2076 |
| 2009/0141861 A1* | 6/2009 | Gaved | ................... | G01N 23/20 |
| | | | | 378/70 |
| 2012/0288058 A1* | 11/2012 | Maeyama | ............ | G01N 23/207 |
| | | | | 378/46 |
| 2014/0185758 A1* | 7/2014 | Kang | .................... | G01N 23/04 |
| | | | | 378/62 |
| 2015/0003578 A1* | 1/2015 | Kim | .................... | G01N 23/046 |
| | | | | 378/20 |
| 2015/0246849 A1* | 9/2015 | Yamashita | ........... | G01N 23/223 |
| | | | | 432/106 |
| 2016/0116424 A1* | 4/2016 | Furukawa | ............ | G01N 23/223 |
| | | | | 378/44 |

\* cited by examiner

> US 9,784,699 B2

QUANTITATIVE X-RAY ANALYSIS—MATRIX THICKNESS CORRECTION

FIELD OF INVENTION

The invention relates to a method of quantitative X-ray analysis and apparatus for carrying out the method.

BACKGROUND TO THE INVENTION

Materials analysis using X-rays provides accurate data in a number of applications and industries. X-ray fluorescence measurements allow the determination of the elemental composition of a sample. In some applications however this is not enough and there is a need not merely to determine the elemental composition but also to determine structure parameters such as the crystalline phases of a sample and X-ray diffraction is used in these cases. Typically, high resolution X-ray diffraction measurements are carried out in reflection mode, where an incoming beam of X-rays is incident on a first surface of a sample and the X-rays diffracted by a diffraction angle 2θ from the same surface of the sample are detected by a detector.

In some applications it is useful to be able take X-ray diffraction measurements in a transmission mode, where the X-rays are incident on a first surface of a sample and diffracted by a diffraction angle 2θ are measured after passing through the sample from the first surface to the opposite second surface.

A problem with making measurements in this transmission geometry is that the sample itself may be absorbing for X-rays. Therefore, it is difficult to carry out accurate quantitative analysis of the diffracted X-rays to determine the amount of any given phase of the sample, since the absorption of X-rays in the sample is not in general known. Small changes in the concentration of various components in the sample can cause significant changes in absorption. This is a problem for quantitative X-ray analysis designed to measure the quantity of a given component in the sample, since the amount of that component is unknown but will affect the absorption.

A yet further problem when measuring pressed powder samples is that the thickness d and density ρ of the pressed pellet, or their more commonly used product $\xi=\rho d$ (known as "mass thickness" or "surface density") is not generally exactly known. A value of the mass thickness can be directly obtained as the ratio of the weight of the pellet to its surface. However, the resulting number is not accurate enough and will introduce large errors in the quantification of the transmission measurements.

Furthermore, in an industrial environment, it will be desired to make a pressed powder sample and then measure it as soon as possible. It is generally undesirable to have to make accurate measurements of mass thickness before carrying out X-ray measurement.

These considerations may be seen with reference to FIG. 1 which illustrates the theoretically calculated diffraction intensity for free lime as a function of sample thickness for three samples of standard cement clinker materials (Portland cement clinker) mixed with a wax binder for various binder percentages of 0%, 10%, 20% and 30%. Note that in spite of the fact that the samples of higher thickness contain more diffracting material—a sample of twice the thickness has twice the amount of free lime—the diffracted intensity is in fact less.

Realistic sample thicknesses (>3 mm) and dilution ratios (10%-20%) that guarantee robust samples in industrial applications are in the highly non-linear regime. This means that a small thickness deviation will have a large effect on the measured or calculated intensities. This is mainly the reason that an estimate of the mass thickness will produce poor results.

Further, as illustrated in FIG. 2, the diffraction intensity is also dependent on the exact composition. FIG. 2 shows three graphs for three different samples each of Portland cement clinker. In spite of the general similarity between the samples, the diffraction intensity still varies from sample to sample illustrating that the effect of absorption is a function of the exact composition which varies from sample to sample. At a thickness of about 3 mm a difference of about 8% in diffraction intensity is seen. This too makes calculating a quantitative measure of free lime concentration from diffraction measurements difficult.

The effects of a variable composition on quantitative measurement is known as matrix correction since it depends on the composition of the measured sample. It is in general difficult to calculate the matrix correction without any information on thickness and composition. There is therefore a need for a measurement method which avoids this difficulty.

Absorption of electromagnetic waves that pass directly through a medium without diffraction may be characterised by the Beer-Lambert law $$I = I_0 e^{-\mu \rho d} \quad (1)$$

Where $I_0$ is the original intensity, I the intensity after passing through the material, μ the mass attenuation coefficient of the material, ρ the material density and d the material thickness (i.e. the ray path length in the material).

Using the simple Beer-Lambert law it is possible to derive the effect of the absorption on the measured X-ray intensity simply by a single value, the value of the product μρd. However, in order to correct measured diffraction intensities for thickness and matrix variations both the product μρd as well as the mass absorption coefficient μ are required. Two samples with the same product μρd but (for example) different μ would appear to have the same attenuation according to a simple Beer-Lambert law but in this application do not give the same intensity of a measured diffraction.

There is therefore a need for a method that quantitatively carries out a thickness and matrix correction for X-ray diffraction.

SUMMARY OF THE INVENTION

According to a first aspect of the invention, there is provided a method of X-ray analysis comprising:

making an X-ray diffraction measurement in transmission by directing X-rays from an X-ray source at the energy E onto a sample at an incident angle $\psi_1$ to the surface of the sample and measuring a measured intensity $I_d(\theta_d)$ of the diffracted X-rays at the energy E with an X-ray detector at an exit angle $\psi_2$ corresponding to an X-ray diffraction peak of a predetermined component;

making a correction measurement of X-rays by measuring the transmitted intensity of X-rays at an energy E transmitted directly through the sample without deviation;

making X-ray fluorescence measurements to determine the elemental composition of a sample; and calculating a matrix corrected X-ray intensity using the measured X-ray intensity in the X-ray diffraction measurement, the correction measurement and the mass attenuation coefficient of the sample calculated from the elemental composition and the mass attenuation coefficients of the elements.

By carrying out measurements in this way, it is possible to correct the diffraction intensity for the effects of the absorption through the sample and hence obtain quantitative measurements even in transmission. The theory of the correction is presented below.

The step of making a correction measurement and the step of making X-ray fluorescence measurements take place at the same time. In this way, the time to complete the measurements for a sample may be reduced as much as possible. The order of measurements can be varied as required.

The product $\mu \rho d$ may be calculated using the Beer-Lambert law from the correction measurement, where $\mu(E)$ is the mass attenuation coefficient, $\rho$ the sample density and d the sample thickness.

The mass attenuation coefficient $\mu(E)$ of the sample may be calculated from the sum for all sample components $$\mu(E) = \sum_{i=1}^{i=nel} w_i \mu_i(E)$$

where $w_i$ is the fraction of a sample component, $\mu_i$ is the mass attenuation coefficient of the respective sample components.

The matrix corrected measurement intensity $I_{dc}$ may be calculated from $$I_{dc} = \frac{I_d(\theta_{fl})}{M_{fl}}$$

with the matrix correction factor $M_{fl}$ calculated by:

$$M_{fl} = \frac{e^{-\mu \cdot \rho \cdot d \cdot \cos ec \, \psi_2} - e^{-\mu \cdot \rho \cdot d \cdot \cos ec \, \psi_1}}{\mu \cdot (\cos ec \, \psi_1 - \cos ec \, \psi_2)}.$$

The method is of particular application to the determination of the amount of free lime in a clinker sample.

The method may include a calibration step. The method may thus comprise:

obtaining a calibration line by carrying out a method as set out above for a plurality of samples having a known concentration of the predetermined component; and measuring the quantity of a predetermined component in an unknown sample by carrying out a method as set out above for the unknown sample.

The calibration may include fitting a straight line to the corrected intensity as a function of the concentration of the plurality of samples having a known concentration of the predetermined component.

In another aspect, the invention relates to an X-ray apparatus, comprising:

a sample stage for supporting a sample extending substantially horizontally;

an X-ray source located on one side of the sample stage;

an X-ray fluorescence X-ray detector;

an diffraction X-ray detector located on the other side of the sample stage for carrying out X-ray diffraction in a transmission geometry; and a controller;

wherein the controller is arranged to cause the X-ray apparatus to carry out a method as set out above.

Such apparatus is capable of making the measurements as set out above.

The X-ray apparatus may include a transmission X-ray detector located above the sample stage for measuring the intensity of X-rays emitted by the X-ray source and passing through the sample without deflection. The transmission X-ray detector can be arranged differently to the diffraction X-ray detector, for example with a different filter and different collimation arrangements, so that the diffraction measurement and transmission measurements can both be separately optimised.

The X-ray source may be a source of Ag Kα radiation.

A filter may be provided between the sample stage and the transmission X-ray detector, the filter filtering out Ag Kb radiation.

The filter may be a stack of (a) Rh or Pd and (b) Ag or other element with an atomic number higher than 47 for filtering out continuum radiation of the tube spectrum.

The X-ray source and the X-ray fluorescence X-ray detector may be provided under the sample stage and the diffraction X-ray detector is provided above the sample stage.

BRIEF DESCRIPTION OF THE DRAWINGS

An example of the invention will now be described with reference to the accompanying diagrams, in which.

DETAILED DESCRIPTION

The invention relates to a method which can be applied for the correction of measured photon intensities in X-ray diffraction in transmission geometry without explicit knowledge of the sample's thickness.

Theory

XRD measurements performed in transmission geometry require that the measured specimens have finite thickness in order to allow the generated photons to escape the specimen from the back side and at a certain exit angle. Theoretical calculations predict that the measured photon intensity will depend both on sample thickness as well as on composition. In that sense the repeatability of the measurements with respect to sample preparation can be highly affected even for specimens prepared from a single sample assuming that a different dilution ratio (binder/material) is applied during sample preparation.

The way in which X-rays pass through the sample is determined by:

$$\mu(E) = \sum_{i=1}^{i=nel} w_i \mu_i(E) \qquad (2)$$

which is the mass attenuation coefficient of the specimen (typically expressed in cm$^2$/g) which is directly related to the composition of the specimen since it contains the weight fractions of all elements in the specimen $w_i$ and the mass absorption coefficient of each element $\mu_i(E)$ at the excitation energy E.

Other relevant definitions used in this and other equations in this document are collected below for convenience:

| | |
|---|---|
| $w_{fl}$ | The weight fraction of the predetermined component |
| $I_d$ | The intensity (kcps) of scattered/diffracted photons recorded by the detector |
| $I_{dc}$ | The intensity (kcps) of scattered/diffracted photons recorded by the detector after matrix and thickness correction |
| $M = \dfrac{e^{-\mu'' \cdot \rho \cdot d} - e^{-\mu' \cdot \rho \cdot d}}{\mu \cdot (\operatorname{cosec}\psi_1 + \operatorname{cosec}\psi_2)}$ | Matrix/thickness correction term |
| $\mu' = \mu \cdot \cos ec\, \psi_1$ | Effective mass absorption coefficient (cm$^2$/g) for the incident photons |
| $\mu'' = \mu \cdot \cos ec\, \psi_2$ | Effective mass absorption coefficient (cm$^2$/g) for the scattered/diffracted photons |
| $\psi_1$ | The angle formed between the direction of the incident photons and the surface of the sample (incident angle). |
| $\psi_2$ | The angle formed between the direction of the diffracted photons and the surface of the sample (exit angle - diffraction angle). |
| $G_{fl}$ | The geometry factor for the diffraction channel |
| $\theta_d$ | Diffraction angle |
| $\sigma$ | Scattering cross section |

Figure 1:
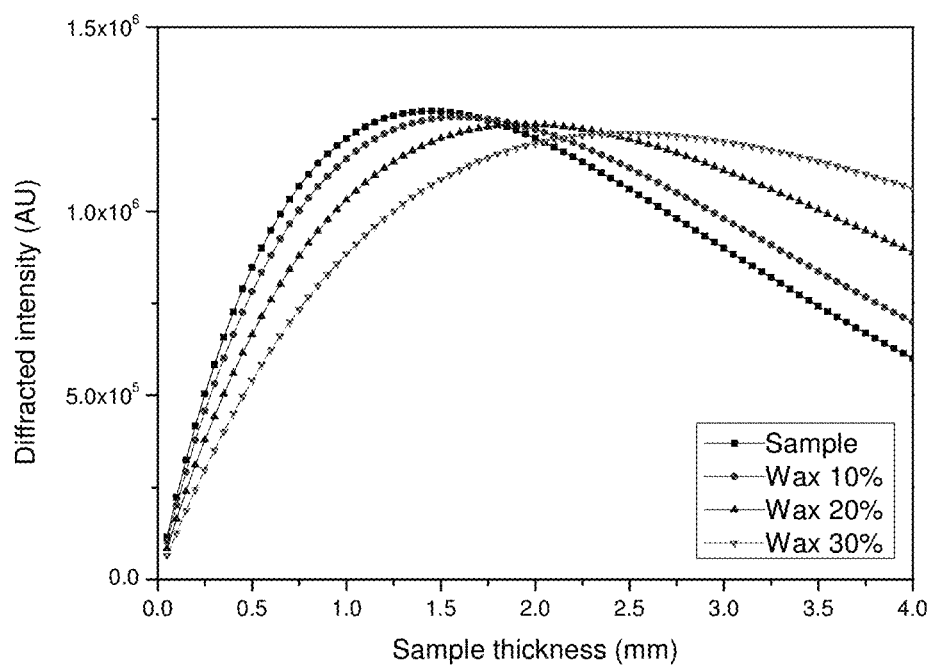
FIG. 1 is a graph of measurement intensity against thickness for samples of different concentrations of powder in wax.
Figure 2:
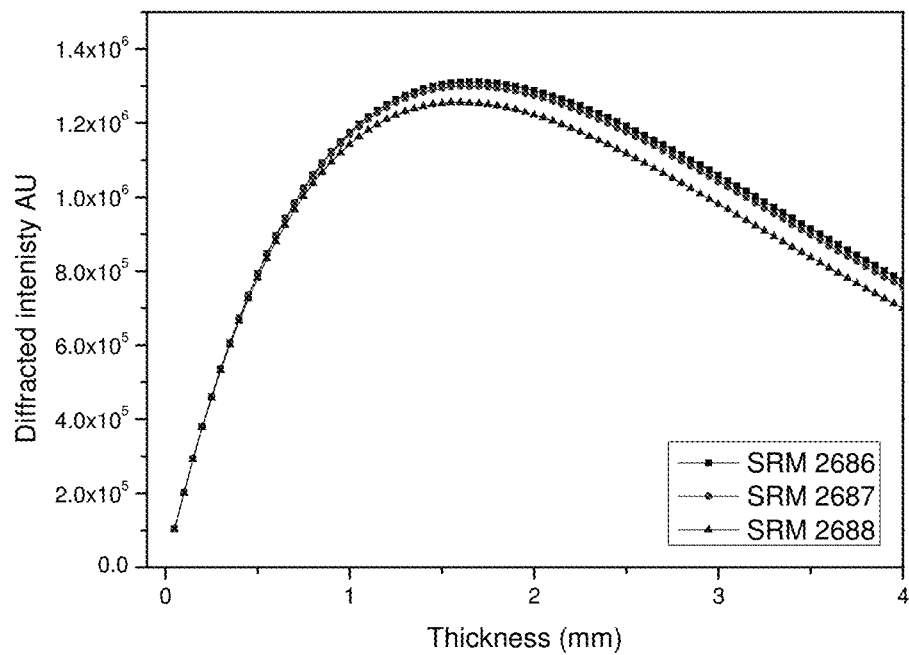
FIG. 2 is likewise a graph of measurement intensity against thickness for samples of different composition.
Figure 3:
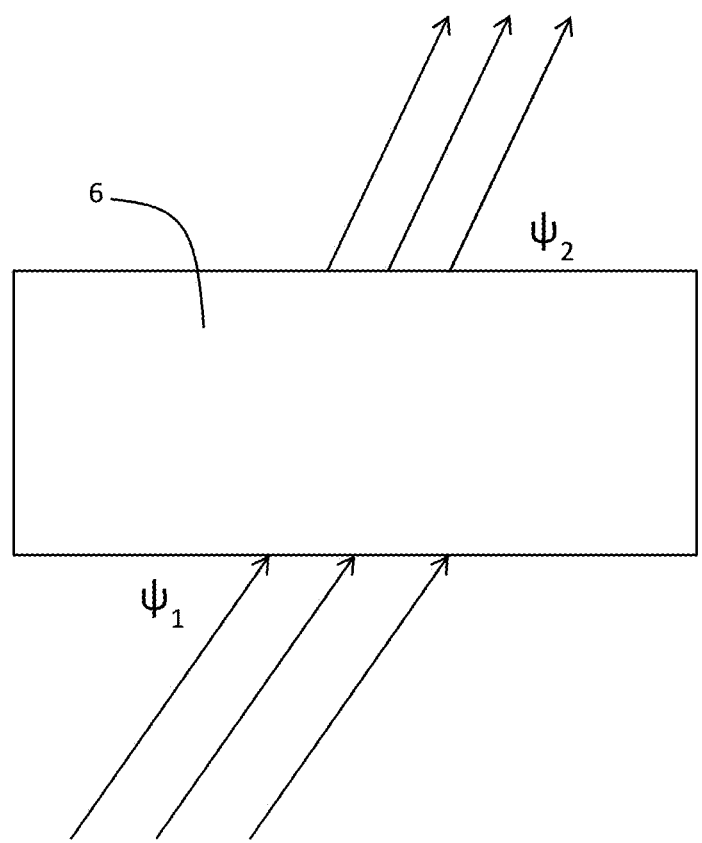
FIG. 3 is a schematic indicating incident and exit X-rays in a configuration considered below in the "theory" section.
Figure 4:
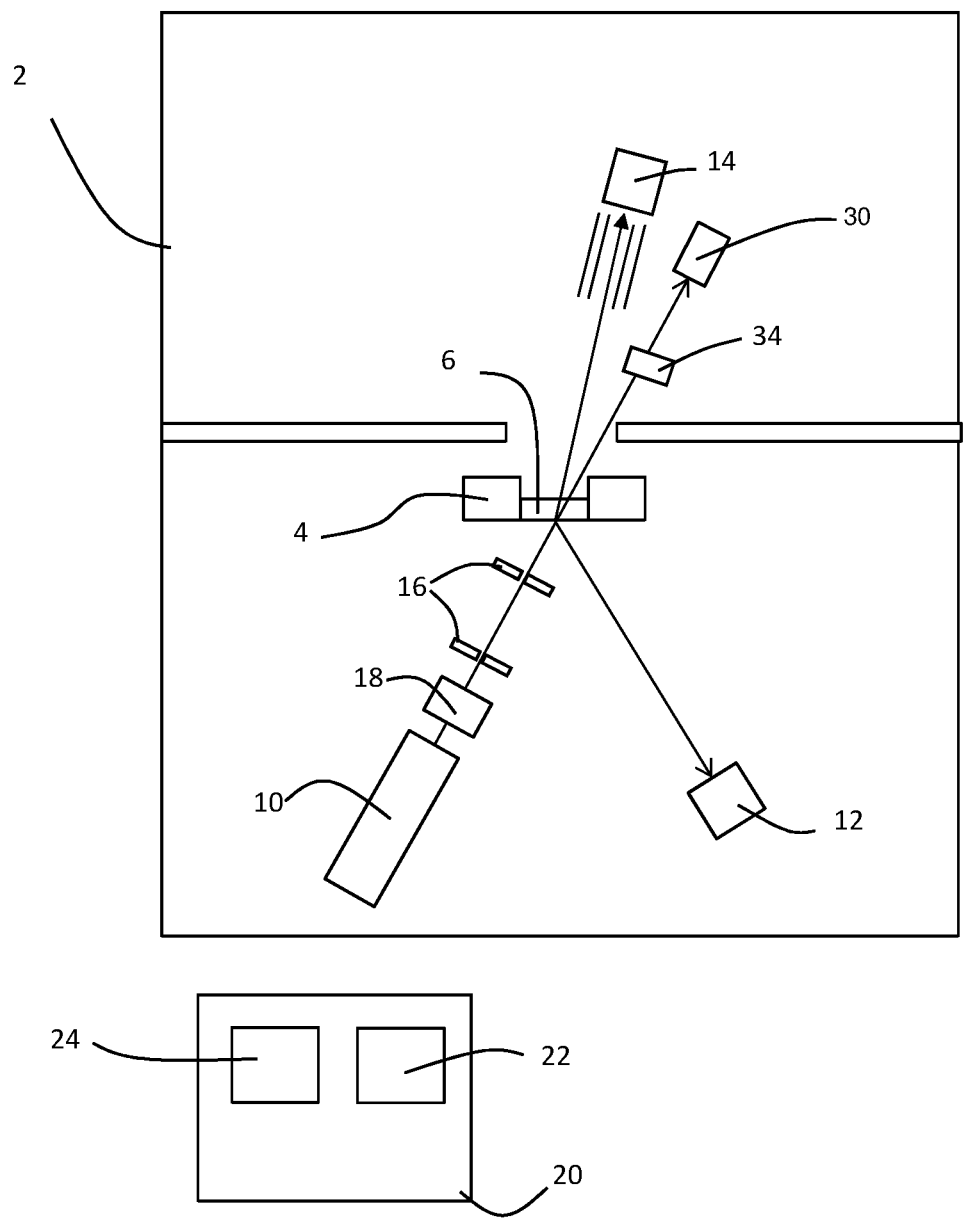
FIG. 4 shows apparatus used to take measurements in a first embodiment of the invention.

Consider X-rays incident on a sample at an incident angle $\psi_1$ and further consider the X-rays diffracted by a particular component at an exit angle $\psi_2$ as illustrated in FIG. 1.

An example will be presented in this section for assistance in understanding the mathematics. In the example the particular (pre-determined) component is free lime though the method is equally applicable to other components. Assuming the incident radiation is the Ag-Ka line then the first order diffraction will be expected to be at a diffraction angle $2\theta_{fl}=13.3°$. Therefore, in this example and assuming an incident angle $\psi_1=57°$ the exit angle $\psi_2=57°+13.3°=70.3°$ for the diffraction peak.

At the exit angle corresponding to the diffraction peak, the intensity that will be observed by the scintillation detector will be given by:

$$I_d(\theta_{fl}) = I_0 \cdot G_{fl} \cdot \operatorname{cosec}\psi_1 \cdot \lfloor w_{fl} \cdot \sigma_{fl}(\theta_{fl}) + (1-w_{fl}) \cdot \sigma_{oth}(\theta_{fl}) \rfloor \cdot M_{fl} \quad (3)$$

Where:

$$M_{fl} = \frac{e^{-\mu \cdot \rho \cdot d \cdot \cos ec\, \psi_2} - e^{-\mu \cdot \rho \cdot d \cdot \cos ec\, \psi_1}}{\mu \cdot (\cos ec\, \psi_1 - \cos ec\, \psi_2)} \quad (4)$$

is the self-absorption term at the angle $\theta_{fl}$.

Note that $\sigma_{fl}$ is the scattering cross section of the predetermined component measured at a diffraction peak and $\sigma_{oth1}$ the scattering cross section of all other components.

This can be written as $$I_{dc} = \frac{I_d(\theta_{fl})}{M_{fl}} = \quad (5)$$

-continued
$$I_0 \cdot G_{fl} \cdot \operatorname{cosec}\psi_1 \cdot w_{fl} \cdot \sigma_{fl}(\theta_{fl}) + I_0 \cdot G_{fl} \cdot \operatorname{cosec}\psi_1 \cdot (1-w_{fl}) \cdot \sigma_{oth}(\theta_{fl})$$

The left hand side of this equation expresses the matrix and thickness corrected diffraction intensity $I_{dc}(\theta_{fl})$.

The second part is the sum of two terms: One term which accounts for the diffraction signal originating from the free lime phase and another term accounting for the influence of other crystalline and amorphous phases. Within a limited range of clinker types this factor can be considered as a constant background and equation (5) can be rewritten as:

$$I_{dc}(\theta_{fl})=K \cdot w_{fl}+I_{bg}(\theta_{fl}) \quad (6)$$

with K being a proportionality constant

In general, evaluating equation (4) is far from straightforward.

However, the inventors have realised that some samples can be sufficiently well characterised by XRF that the composition of elements can be determined. Then, equation (2) can be used since the absorption $\mu$ is simply a sum of the absorption and is determined by the known compounds present in the sample. This leads to a value $\mu$.

It is also possible to calculate the product $\mu\rho d$ by carrying out measurements of direct transmission with and without the sample and using the Beer-Lambert law of equation (1). Alternatively, and instead of measuring the direct beam which can saturate the detector, the transmitted radiation can be measured through a well characterized standard of appropriate thickness (for example Quartz glass). Then, the ratio of the two transmission experiments is formed and the unknown $\mu\rho d$ of the sample is determined relative to the corresponding one of the standard.

With these two pieces of information it is possible to correct the measured intensity of an XRD measurement by a matrix intensity correction M, i.e. to correct the measured value for the effects of absorption by other elements in the sample by substituting these values in equation (4).

Thus, after calibration of the instrument for an XRD line corresponding to a particular component, it is possible to correct for absorption in the sample and obtain $I_{dc}(\theta_{fl})$ from equation (5). From this value and by using the calibration curve the weight fraction of a particular component can be determined.

Implementation

An X-ray apparatus 2 has a sample stage 4 for holding a sample 6.

In practice, this apparatus 2 is a conventional XRF apparatus with an X-ray source 10 mounted below the sample stage 4. In this embodiment there is a fluorescence X-ray detector 12 for measuring X-ray fluorescence below the sample stage 4. The fluorescence X-ray detector may be an energy dispersive detectors measuring X-ray intensity as a function of energy or a wavelength dispersive X-ray detector with a crystal for selecting X-rays only of a particular wavelength. The crystal may be movable to allow selection of different wavelengths or fixed to allow measurement of a particular wavelength of interest.

To the conventional XRF apparatus is added a transmission X-ray detector 14 which is mounted above the sample stage 4 on a goniometer so that it can measure diffracted X-rays as a function of angle. A correction X-ray detector 30 is provided adjacent to the transmission X-ray detector as will be described below.

A number of other components are provided, including collimator 16 and filter 18.

The apparatus is under control of controller 20 which includes a memory 22 and processor 24.

In the embodiment shown, the X-ray source 10 is arranged to emit Ag-Ka radiation and the filter 18 is arranged to filter out the Ag-Kb line and possibly also to filter out continuum radiation. The filter may be a multilayered filter including layers of Rh or Pd to filter out the Ag-Kb line and other layers such as Ag to filter out the continuum. Other high atomic number (Z) layers may be used as well as the Ag or additional to the Ag.

For the diffraction measurement a parallel plate collimator 16 placed between source and sample is used. For the correction measurement simple pinhole optics between sample and detector 30 may be used for collimation.

In use, a sample 6 is prepared by the pressed powder method. A powder is compressed together with wax binder in a ring to form a sample which is mounted on the sample stage. In the specific example, the sample is a clinker sample and the predetermined component which is to be measured is free lime.

In a first stage of measurement, the X-rays source is activated (by removing a shutter) and X-rays are incident on a sample. In this case, XRF measurements are made by the fluorescence X-ray detector. The correction X-ray detector 30 is arranged so that it is directly in line with the incident X-rays, i.e. it detects directly transmitted X-rays. The correction X-ray detector measures the intensity of X-rays passing through the sample and hence the absorption in the sample.

In order to avoid detector overloading and to ensure that the radiation recorded by the detector 30 is identical to the one used for the diffraction measurements an Ag filter 34 of appropriate thickness is placed between the sample and the detector to filter out the Ag-Kb line and possibly also to filter out continuum radiation. The filter may be a multilayered filter including layers of Rh or Pd to filter out the Ag-Kb line and other layers such as Ag to filter out the continuum A measurement of the intensity at the diffraction peak $2\theta_{fl}=13.3°$ is then measured in transmission with the source located to provide an incident angle $\psi_1=57°$ and the transmission X-ray detector located to provide an exit angle $\psi_2=57°+13.3°=70.3°$.

This information is then put together using equations (1) to (4) to obtain not merely information about the specific elements (obtained by XRF) but also one or more phases (obtained only by XRD).

These measurements and the calibration are all carried out controlled by code stored in memory 24 which controls processor 22 in controller 20 to control the apparatus 2 to carry out the measurements.

Those skilled in the art will realise that the apparatus and method may be varied to suit the specific equipment available. For example, a different X-ray source with a different radiation spectrum may be used. It may be possible to use the same detector for the diffraction measurements and transmission measurements in place of detectors 14, 30.

EXAMPLES

Figure 5:
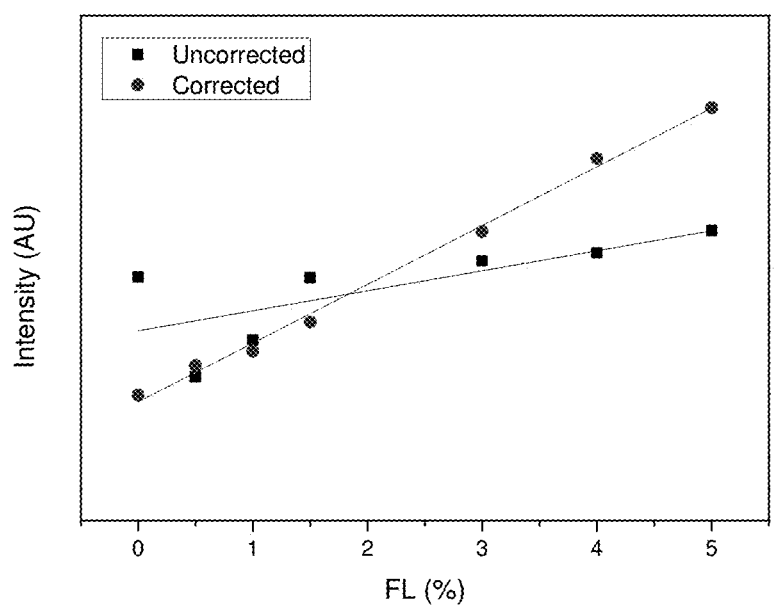
FIG. 5 shows some results measured using the invention.

An experimental example was carried out to test the validity of the approximations made, as well as the applicability of the method. A set of pressed pellets was made from a clinker matrix spiked with appropriate free lime (FL) quantities to yield final FL concentrations equal to 0%, 0.5% 1%, 1.5%, 2%, 3%, 4% and 5%. According to equation (6) it is possible to construct a calibration line which relates the corrected diffraction intensities with the concentration of the FL. The results are shown in FIG. 5.

For comparison the uncorrected intensities are also plotted as function of the FL concentration. Note that the application of the correction improves the quality of the calibration line considerably. There is much less variability and the gradient of the line is steeper which makes accurate intensity measurement possible.

We claim:

1. A method of X-ray analysis comprising:
   making an X-ray diffraction measurement in transmission by directing X-rays from an X-ray source at the energy E onto a sample at an incident angle $\psi_1$ to the surface of the sample and measuring a measured intensity $I_d(\theta_{fl})$ of the diffracted X-rays at the energy E with an X-ray detector at an exit angle $\psi_2$ corresponding to an X-ray diffraction peak of a predetermined component
   making a correction measurement of X-rays by measuring the transmitted intensity of X-rays at an energy E transmitted directly through the sample without deviation;
   making X-ray fluorescence measurements to determine the elemental composition of a sample; and
   calculating a matrix corrected X-ray intensity using the measured X-ray intensity in the X-ray diffraction measurement, the correction measurement and the mass attenuation coefficient of the sample calculated from the elemental composition and the mass attenuation coefficients of the elements, and wherein the matrix corrected measurement intensity $I_{dc}$ is calculated from $$I_{dc} = \frac{I_d(\theta_{fl})}{M_{fl}}$$

with the matrix correction factor $M_{fl}$ calculated by:

$$M_{fl} = \frac{e^{-\mu \cdot \rho \cdot d \cdot \cos ec\, \psi_2} - e^{-\mu \cdot \rho \cdot d \cdot \cos ec\, \psi_1}}{\mu \cdot (\cos ec\, \psi_1 - \cos ec\, \psi_2)}$$

using the product $\mu \rho d$ calculated from the correction measurement and the mass attenuation coefficient $\mu$ of the sample calculated from the elemental composition determined from the X-ray fluorescence measurements.

2. The method according to claim 1, wherein the step of making a correction measurement and the step of making X-ray fluorescence measurements take place at the same time.

3. The method according to claim 1, comprising calculating the product $\mu \rho d$ from the correction measurement using the Beer-Lambert law, where $\mu$ is the mass attenuation coefficient at the energy E, $\rho$ the sample density and d the sample thickness.

4. The method according to claim 1 comprising calculating the mass attenuation coefficient $\mu(E)$ of the sample from the sum for all sample components:

$$\mu(E) = \sum_{i=1}^{i=nel} w_i \mu_i(E)$$

where $w_i$ is the fraction of a sample component, and $\mu_i$ is the mass attenuation coefficient of the respective sample components.

5. The method according to claim 1 wherein the predetermined component is free lime.

6. A method comprising:
obtaining a calibration line by carrying out a method according to claim 1 for a plurality of samples having a known concentration of the predetermined component; and
measuring the quantity of a predetermined component in an unknown sample by carrying out a method according to claim 1 for the unknown sample.

7. The method according to claim 6 wherein obtaining a calibration line comprises fitting a straight line to the corrected intensity as a function of the concentration of the plurality of samples having a known concentration of the predetermined component.

8. An X-ray apparatus, comprising:
a sample stage for supporting a sample extending substantially horizontally;
an X-ray source located on one side of the sample stage;
an X-ray fluorescence X-ray detector;
an diffraction X-ray detector located on the other side of the sample stage for carrying out X-ray diffraction in a transmission geometry; and
a controller;
wherein the controller is arranged to cause the X-ray apparatus to carry out a method according to any preceding claim.

9. The X-ray apparatus according to claim 8, further comprising a transmission X-ray detector located above the sample stage for measuring the intensity of X-rays emitted by the X-ray source and passing through the sample without deflection.

10. The X-ray apparatus according to claim 8 wherein the X-ray source is a source of Ag Ka radiation.

11. The X-ray apparatus according to claim 8 in which the X-ray source and the X-ray fluorescence X-ray detector are provided under the sample stage and the diffraction X-ray detector is provided above the sample stage.

12. The X-ray apparatus according to claim 10 further comprising a filter between the sample stage and the diffraction X-ray detector for carrying out X-ray diffraction in a transmission geometry, the filter filtering out Ag Kb radiation.

13. The X-ray apparatus according to claim 12 wherein the filter is a stack of (a) Rh or Pd and
(b) Ag or other element with an atomic number higher than 47 for filtering out continuum radiation of the tube spectrum.

* * * * *